(12) United States Patent
Mehmanesh

(10) Patent No.: US 8,585,572 B2
(45) Date of Patent: Nov. 19, 2013

(54) CARDIAC ASSIST DEVICE

(75) Inventor: Hormoz Mehmanesh, Tehran (IR)

(73) Assignee: Surgery In Motion, Ltd, London (GB)

( * ) Notice: Subject to any disclaimer, the term of this patent is extended or adjusted under 35 U.S.C. 154(b) by 281 days.

(21) Appl. No.: 12/452,697

(22) PCT Filed: Jul. 18, 2008

(86) PCT No.: PCT/EP2008/005916
§ 371 (c)(1),
(2), (4) Date: Apr. 1, 2010

(87) PCT Pub. No.: WO2009/010302
PCT Pub. Date: Jan. 22, 2009

(65) Prior Publication Data
US 2010/0197994 A1     Aug. 5, 2010

(30) Foreign Application Priority Data
Jul. 18, 2007   (EP) .................................... 07014120

(51) Int. Cl.
*A61N 1/362* (2006.01)
(52) U.S. Cl.
USPC ........................................................... 600/18
(58) Field of Classification Search
USPC .................................................. 600/118, 18
See application file for complete search history.

(56) References Cited

U.S. PATENT DOCUMENTS

| | | | | |
|---|---|---|---|---|
| 4,957,504 | A * | 9/1990 | Chardack | 623/3.14 |
| 6,210,318 | B1 * | 4/2001 | Lederman | 600/18 |
| 2004/0152945 | A1 * | 8/2004 | Kantrowitz et al. | 600/18 |

FOREIGN PATENT DOCUMENTS

| WO | WO 00/35515 | 6/2000 |
|---|---|---|
| WO | WO 2006/067473 | 6/2006 |

OTHER PUBLICATIONS

Rose et al, Long-Term Use of a Left Ventricular Assist Device for End-Stage Heart Failure, 2001, pp. 1435 to 1443, The New England Journal of Medicine, vol. 345, No. 20.
Deng, Advanced Heart Failure Therapy With Mechanical Circulatory Support Devices (MCSC), 2002, pp. 1-7; HF—Contakt News.
Joshi, Artificial Heart Research: An Historical Perspective, 2001, pp. 1-44.
Saito et al, End-organ Function During Chronic Nonpulsatile Circulation, 2002, vol. 74, pp. 1080 to 1085; The Annals of Thoracic Surgery.
Frazier et al, Clinical Left Heart Assist Devices: A Historical Perspective, 2000; Chapter 1, pp. 3 to 13, from *Cardiac Assist Devices*, Futura Publishing Co. Inc., Armonk, NY.

(Continued)

*Primary Examiner* — Christopher D Koharski
*Assistant Examiner* — Nadia Ahmad
(74) *Attorney, Agent, or Firm* — Fattibene and Fattibene LLC; Paul A. Fattibene

(57) ABSTRACT

A cardiac assist device (100) comprises a stent 103, 403) which is implantable into a blood vessel of a patient. The stent (103, 403) encloses an inner volume (119, 419). At least one inflatable element (104, 409-413) is attached to the stent (103). The at least one inflatable element (104, 409-413) is provided in the inner volume (119, 419) of the stent (103, 403), wherein the ai least one inflatable element (104, 409-413) annularly encloses a central opening (118, 418) being parallel to a longitudinal axis of said stent (103, 403). The cardiac assist device (100) further comprises a fluid supply adapted for periodically inflating and deflating the at least one inflatable element (104, 409-413), wherein said fluid supply comprises at least one fluid supply line (105, 405) connectable to the at least one inflatable element (104, 409-413) and implantable into a blood vessel of the patient.

26 Claims, 7 Drawing Sheets

(56) References Cited

OTHER PUBLICATIONS

Hendry et al, The HeartSaver Left Ventricular Assist Device: an Update, 2001, vol. 71, pp. 166 to 170, The Annals of Thoracic Surgery.

Cooley, Mechanical Circulatory Support System: Past, Present, and Future, 1999, vol. 68, pp. 641 to 642, The Annals of Thoracic Surgery.

DeBakey, The Odyssey of the Artificial Heart, 2000, vol. 24(6), pp. 405 to 411, Artificial Organs.

Mussivand et al, Progress with the HeartSaver Ventricular Assist Device, 1999, vol. 68, pp. 785 to 789, The Annals of Thoracic Surgery.

\* cited by examiner

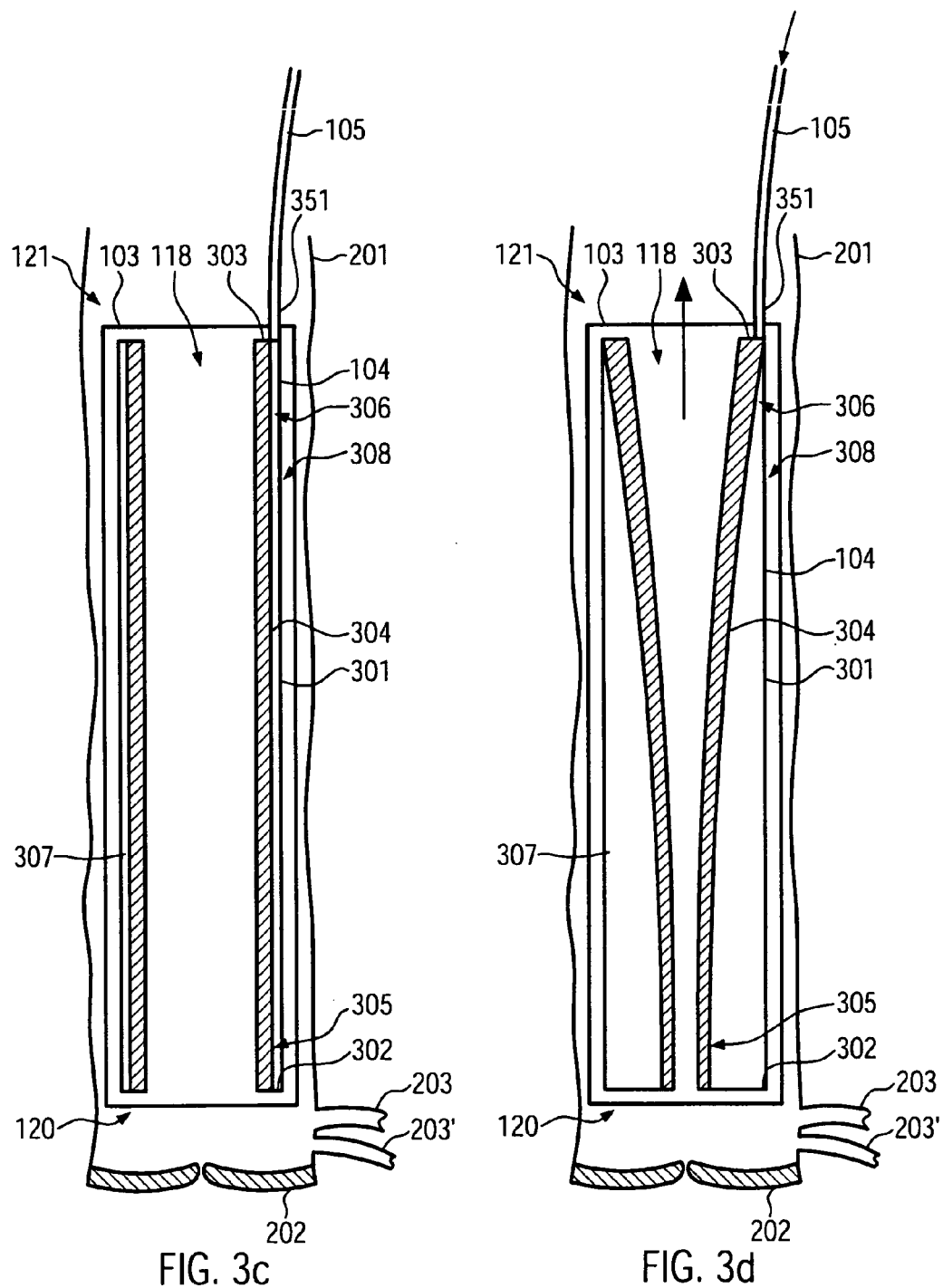

_US 8,585,572 B2_

CARDIAC ASSIST DEVICE

FIELD OF THE INVENTION

The present invention generally relates to the filed of cardiac assist devices, in particular to a cardiac assist device which may be implanted at least partially into a blood vessel of a patient to assist the heart of the patient in pumping blood through the circulatory system, to decrease the afterload of the heart, to increase the native ejection fraction and/or to improve the coronary perfusion and the oxygen supply to the myocardium.

BACKGROUND OF THE INVENTION

In patients suffering from heart failure which may, for example, be caused by a myocardial infarction, a dilatative or ischemic cardiomyopathy or another disease, the capability of the heart to pump blood through the patient's circulatory system may be reduced to a large extent. Hence, blood supply to vitally important organs may be reduced, which may directly or indirectly lead to death of the patient.

Heart failure may be treated by means of a heart transplantation, wherein the patient's heart is replaced by a donor heart which is obtained from a brain dead person. Transplant organs, however, may be rare, and a careful selection of the transplant organ is required in order to avoid a rejection of the transplant organ by the immune system of the patient. Hence, a considerable amount of time may pass until a transplant organ suitable for the patient can be found, which amount of time may be too long to save the patient's live. More than 50% of the candidates for a heart transplantation die while they are registered on the waiting lists for a heart transplantation. Furthermore, there are many contraindications for heart transplantation such as old age, infections and longstanding high pulmonary pressure.

Therefore, it has been proposed to replace or assist the patient's heart by mechanical devices, at least temporarily while the patient is waiting for a suitable donor ("bridge to transplant"). Besides artificial hearts, which are designed to completely replace the patient's heart, cardiac assist devices have been proposed which support the action of the native heart.

In one example of a cardiac assist device according to the state of the art, an atrium of the patient's heart may be cannulated, and the cannula may be connected to a pump. Thus, blood can be pumped out of the atrium, and may be injected into a further cannula connected to an artery of the patient, wherein the artery chosen depends on whether the left or the right ventricle is supported by the cardiac assist device. The right ventricle of the heart may be supported by cannulating the right atrium and the pulmonary artery. The left ventricle may be assisted by cannulating the left atrium and the aorta.

A problem of cardiac assist devices according to the state of the art is that connecting the cardiac assist device to the circulatory system of the patient may require open heart surgery, which may imply a high risk of complications.

WO 00/35515 discloses an intravascular cardiac assist device that comprises an elongated tubular member adapted for insertion into a blood vessel, such as a pulmonary artery, the tubular member comprising a lumen defining a perfusion path within the vessel through the tubular member, an inlet port, an outlet port, an optional inlet valve associated with the inlet port and an optional outlet valve associated with the outlet port, and an inflatable member positioned in the lumen and selectively movable between a deflated position and one or more inflated positions during which blood is propelled from the inlet port axially through the lumen and back into the vessel through the outlet port and the optional outlet valve. The device is implanted through an incision in the blood vessel, and fluid is supplied to the inflatable member by means of a flexible inflation/deflation lumen inserted through the incision.

A problem of the intravascular cardiac assist device disclosed in WO 00/35515 is that the incision in the blood vessel, which is required to inflate and deflate the inflatable member, limits the application of the device to providing cardiac assist during heart surgery, and for providing post-operative support. However, the device is not suitable for providing cardiac assist for a longer period of time, for example until a donor heart for the patient is available.

WO 00/53240 discloses a balloon pump system including a catheter-mounted pumping balloon configured to be positioned within a desired body passageway to pump a fluid, for example blood, through the body passageway. A stent is percutaneously deployed within the body passageway. The pumping balloon is percutaneously deployed within the stent such that the stent is interposed between the pumping balloon and the walls of the body passageway.

A problem of the system disclosed in WO 00/53240 is that the pumping balloon provides an obstacle to fluid flow through the body passageway, even if the balloon is in its deflated state. Moreover, in the deflated state of the balloon, the balloon may have an irregular surface. Thus, turbulences may be created in the blood flow, which may lead to the formation of thrombi. It has been observed that the formation of thrombi may start within about 24 hours after the implantation of a balloon pump, and may lead to a significant risk of complications within about two weeks after the implantation of the balloon pump. Such complications may include peripheral thrombosis, infections, dysfunctions of the balloon pump, and embolism. Therefore, the device of WO 00/53240 may be used only for a relatively short period of time in exceptional situations.

It is an object of the present invention to provide a cardiac assist device which may assist the patient's heart, and which may be used without there being a requirement of open heart surgery for implantation of the device.

It is a further object of the present invention to provide a cardiac assist device which may be used for a relatively long period of time for providing a bridge to transplant, and for providing cardiac assist for an extended period of time to patients wherein counterindications such as old age, infections and longstanding high pulmonary pressure make a heart transplant difficult or almost impossible.

SUMMERY OF THE INVENTION

According to the present invention, this problem is solved by a cardiac assist device comprising a stent. The stent is implantable in a blood vessel of a patient and encloses an inner volume. At least one inflatable element is attached to the stent. The inflatable element is provided in the inner volume of the stent, and annularly encloses a central opening being parallel to a longitudinal axis of the stent. The cardiac assist device further comprises a fluid supply adapted for periodically inflating and deflating the at least one inflatable element. The fluid supply comprises at least one fluid supply line connectable to the at least one inflatable element and implantable into a blood vessel of the patient.

The cardiac assist device can be implanted in a blood vessel of the patient such as, for example, into the aorta or pulmonary artery. For this purpose, the stent can be provided in a collapsed state and the at least one inflatable element can be provided inside the stent in a deflated state. The stent may be connected to a catheter, and may be enclosed by a sheath adapted to prevent a premature expansion of the stent. The catheter, together with the stent and the at least one inflatable element connected thereto, may then be inserted into a blood vessel of the patient, for example a peripheral artery, by means of the Seldinger technique, which is well known to persons skilled in the art. Thereafter, the catheter may be advanced to the aorta or pulmonary artery of the patient. Then, the sheath can be removed to effect an expansion of the stent. The stent may attach to the inner surface of the blood vessel of the patient. Subsequently, the at least one inflatable element may be connected to the fluid supply to be periodically inflated and deflated. The periodic inflation and deflation of the inflatable element may induce or enhance a blood flow through the patient's blood vessel, thus supporting the cardiac action of the patient's heart. Hence, the implantation of the cardiac assist device can be performed in a minimally invasive manner.

The inflatable element which annularly encloses the central opening may exhibit a force to the flowing blood in a substantially radially symmetrical manner. Thus, the flow of blood through the cardiac assist device may be improved. In particular, the annular inflatable element, in its deflated state may have a significantly reduced resistance to blood flow compared to a balloon as described in WO 00/53240. Thus, the risk of complications such as peripheral thrombosis, infections, dysfunctions of the balloon pump, and embolism may be reduced significantly, which may allow to provide cardiac assist for an extended period of time.

The at least one inflatable element may comprise an elastic envelope. The elastic envelope can comprise an inner circumferential portion enclosing the central opening. The inner circumferential portion may have a higher degree of elasticity adjacent a first end of the stent than adjacent a second end of the stent. Thus, in case the inflatable element is inflated by supplying fluid to the inflatable element, at the beginning of the inflation process, the inflatable element may expand to a greater extent in the vicinity of the first end of the stent. In the vicinity of the second end of the stent, due to the lower degree of elasticity of the inner circumferential portion, a higher pressure may be required to expand the inflatable element. Therefore, the inflatable element may first expand at the first end of the stent. If the inflatable element is deflated, the inflatable element will contract to a greater extent in the vicinity of the second end of the stent, since the portion of the elastic envelope having a lower degree of elasticity provides a greater reset force. Thus, the inflatable element may impart a directional motion to the volume of blood inside the cardiac assist device. The cardiac assist device may be implanted such that the first end of the stent is provided closer to the heart (proximal valvular site) of the patient than the second end. Hence, during the inflation, a column of blood inside the cardiac assist device may be pushed away from the patient's heart into the circulatory system. During the deflation, blood may be drawn out of the heart into the cardiac assist device. Thus, the pumping action of the heart can be supported in an efficient manner.

In one embodiment, the inner circumferential portion of the elastic envelope may have a smaller thickness adjacent the first end of the stent than adjacent the second end of the stent. Thus, a higher degree of elasticity adjacent the first end of the stent than adjacent the second end of the stent can be provided in a convenient manner.

In other embodiments, the at least one inflatable element may comprise a plurality of inflatable elements, and the fluid supply can be adapted to successively inflate the plurality of inflatable elements and to successively deflate the plurality of inflatable elements. Due to the successive inflation and deflation, respectively, of the inflatable elements, a directionality may be imparted to the flow of blood, which may allow a particularly efficient support of the pumping action of the patient's heart.

The fluid supply can be adapted to individually inflate and deflate each of the plurality of inflatable elements. Hence, the shape of the space inside the cardiac assist device which is filled with blood and emptied during the deflation and inflation, respectively, of the inflatable elements may be controlled in a particular efficient manner to adapt the action of the cardiac assist device to the individual needs of the patient.

The cardiac assist device may further comprise a heartbeat detector adapted to detect a cardiac action of the patient. Thus, the cardiac action of the patient may be monitored to adapt the operation of the cardiac assist device to the patient's heartbeat. The heartbeat detector may, in some embodiments, comprise a flow sensor, a pressure sensor and/or an electrocardiogram sensor.

The fluid supply can be adapted to synchronize the periodic inflation and deflation of the at least one inflatable element with the cardiac action of the patient. Thus, the at least one inflatable element can be deflated during systole to cause a vacuum in the flow direction which may support an unloading of the ventricle of the patient's heart. During diastole, the inflatable element can be inflated to eject the blood in the flow direction. Additionally, blood may be ejected into the coronary arteries of the patient. This may help to improve a supply of oxygen to the heart.

In some embodiments, the fluid supply may comprise at least one pump. The at least one fluid supply line may connect the at lest one pump and the at least one inflatable element. The fluid supply may further comprise a control unit adapted to control the pump to provide the periodic inflation and deflation of the inflatable element and a power supply connected to the at least one pump and the control unit. Hence, fluid may be pumped into the at least one inflatable element via the at least one fluid supply line by means of the pump to inflate the at least one inflatable element. Additionally, the pump and the at least one fluid supply line may be employed to pump fluid out of the at least one inflatable element in order to deflate the at least one inflatable element. Energy for the operation of the pump and the control unit can be provided by the power supply.

The fluid supply can be implantable into the patient. An implantation of the fluid supply into the patient may help to avoid a risk of infections for the patent, since fluid supply lines and/or electric lines leaving the body of the patient which may allow germs to enter the body of the patient may be avoided. Additionally, the mobility of the patient may be improved, since the patient does not have to be connected to an external device. Fluid supply lines provided in blood vessels of the patient may allow to provide the fluid supply in another part of the patient's body than the stent and the inflatable element. Thus, the fluid supply can be implanted into a part of the patient's body which is easily accessible by surgery and wherein a sufficient amount of space is available. For example, the fluid supply may be implanted pectorally.

The power supply may comprise a rechargeable battery and an induction coil subcutaneously implantable into the patient for recharging the rechargeable battery. The rechargeable battery may provide a power supply which is independent of external power sources. Via the induction coil, the rechargeable battery can be recharged in a convenient manner without requiring an electric line through the patient's skin which might allow germs to enter the patient's body.

The fluid supply may further comprise a fluid reservoir. In the fluid reservoir, fluid which is pumped out of the at least one inflatable element during the deflation of the at least one inflatable element may be stored until the at least one inflatable element is inflated. Additionally, fluid from the fluid supply may be used to balance losses which may be caused, for example, by diffusion through the walls of the at least one inflatable element or other leakages.

In some embodiments, the stent may have a length in a range from about 80 mm to about 100 mm and a diameter in a range from about 25 mm to about 45 mm. Hence, the dimensions of the stent in the expanded state may be adapted for insertion into the patient's aorta and/or pulmonary artery.

The stent may be self-expandable. Due to the individual variation of the diameter of the aorta, a self-expandable stent may fit better to the patient's aorta, and may help to reduce a risk of a rupture of the aorta.

In some embodiments, the at least one inflatable element comprises an elastic envelope that comprises an inner circumferential portion enclosing the central opening, an outer circumferential portion attached to the stent and a first and a second cover portion connecting the inner circumferential portion and the outer circumferential portion. The at least one fluid supply line is attached to the second cover portion. Thus, the fluid supply line may extend from the elastic envelope into a direction substantially parallel to the blood vessel into which the cardiac assist device is implanted, without there being a necessity to strongly bend the fluid supply line. This may facilitate the implantation of the fluid supply line into the blood vessel, and may reduce a resistance of the fluid supply line for fluid flow.

In some embodiments, an area of the second cover portion adjacent the at least one fluid supply line is substantially perpendicular to the longitudinal axis of the stent, at least in an inflated state of the at least one inflatable element. A portion of the at least one fluid supply line adjacent the second cover portion can be substantially parallel to the longitudinal axis of the stent.

In some embodiments, the stent has a collapsed configuration and an expanded configuration. The cardiac assist device further comprises a catheter running through the central opening of the stent and a removable sheath. The sheath is adapted to maintain the stent in the collapsed configuration, wherein the at least one fluid supply line is running through the sheath. The catheter is adapted for being removed after removal of the sheath. As already detailed above, the sheath and the catheter may be used to implant the cardiac assist device in a minimally invasive manner. A method of providing cardiac assist to a patient according to the present invention comprises providing an endovascular portion of a cardiac assist device comprising a stent enclosing an inner volume, at least one inflatable element being attached to the stent and provided in the inner volume of the stent, and a fluid supply line. The at least one inflatable element annularly encloses a central opening parallel to a longitudinal axis of the stent. The endovascular portion is implanted into the patient, wherein the stent and the at least one inflatable element are provided in one of an aorta and a pulmonary artery of the patient. The fluid supply line extends from the one of the aorta and the pulmonary artery to a peripheral blood vessel of the patient. An extravascular portion of the cardiac assist device comprising a fluid supply is provided. The at least one fluid supply line is connected to the extravascular portion. The fluid supply is operated to periodically inflate and deflate the at least one inflatable element.

In some embodiments, the extravascular portion may be implanted into the patient.

In some embodiments, at least a part of the extravascular portion may be pectorally implanted into the patient.

In some embodiments, a donor heart may be transplanted into the patient some time after the implantation of the endovascular portion. The cardiac assist device may be operated until the transplantation of the donor heart.

In some embodiments, the cardiac assist device is operated for at least two weeks.

In some embodiments, a catheter running through the central opening of the inflatable element and through the stent is provided. A sheath is provided over the endovascular portion. The sheath is adapted to maintain the stent in a collapsed configuration. The at least one fluid supply line is running through the sheath. The implantation of the endovascular portion comprises inserting the catheter into the peripheral blood vessel of the patient. The catheter is advanced to the one of the aorta and the pulmonary artery. The sheath is withdrawn to expose the endovascular portion. The stent is expanded into an expanded configuration and the catheter is retraced.

In some embodiments, the sheath is retracted further to expose the fluid supply line.

BRIEF DESCRIPTION OF THE DRAWINGS

Embodiments of the present invention will now be described with reference to the accompanying drawings, wherein:

FIGS. 3a to 3d show schematic cross-sectional view of an aorta comprising a cardiac assist device in stages of a method of operating a cardiac assist device according to an embodiment of the present invention.

DETAILED DESCRIPTION OF THE PREFERRED EMBODIMENTS

Figure 1:
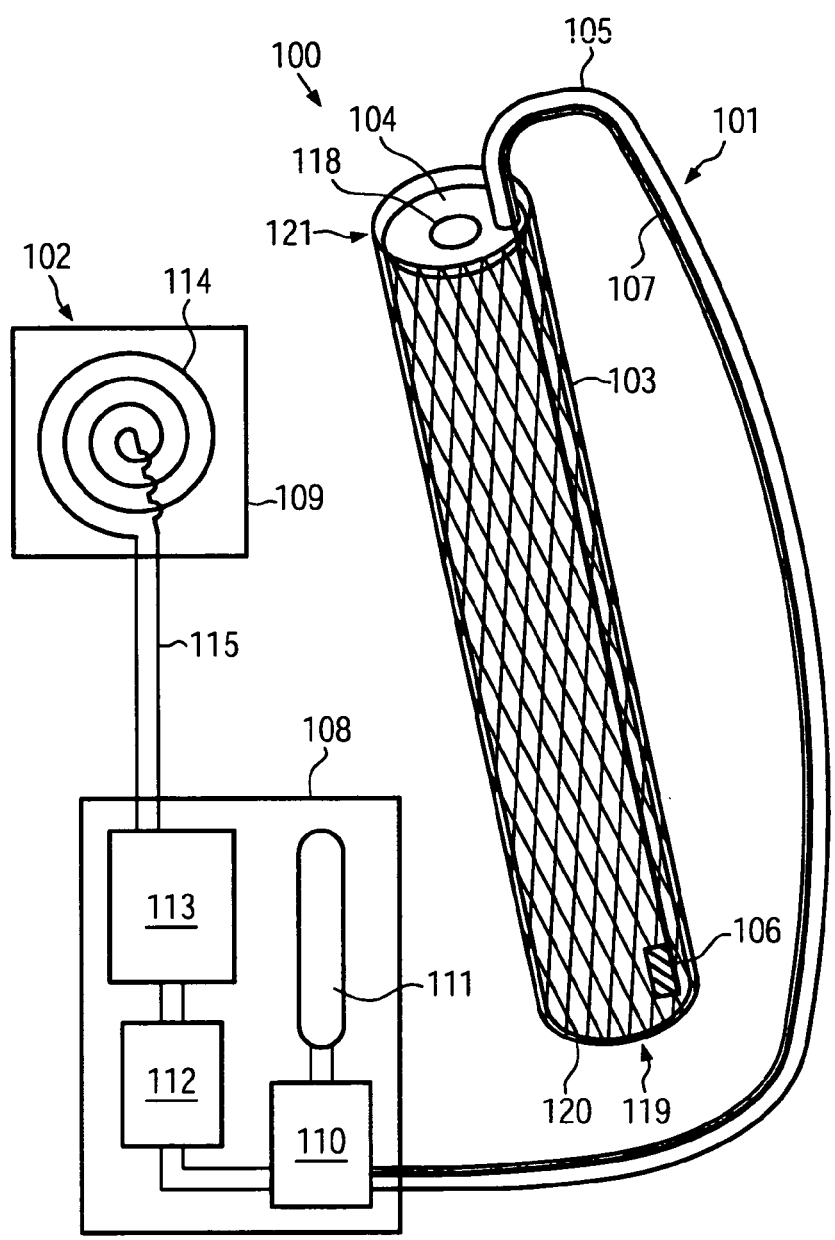
FIG. 1 shows a schematic perspective view of a cardiac assist device according to an embodiment of the present invention.

FIG. 1 shows a schematic cross-sectional view of a cardiac assist device 100 according to an embodiment of the present invention. The cardiac assist device 100 comprises an endovascular portion 101 and an extravascular portion 102. The endovascular portion 101 is configured for implantation into a blood vessel of a patient. The extravascular portion 102 may be configured for implantation into other portions of a patient's body.

The endovascular portion 101 comprises a stent 103. Similar to stents adapted for the treatment of aortic dissections known to persons skilled in the art, the stent 103 may comprise a wire arranged in a zigzag configuration and/or forming a grating, mesh and/or ring and comprising a metal such as, for example, a stainless steel alloy, a cobalt chrome alloy, titanium, tantalum, platinum or gold. In other embodiments, the stent 103 can comprise a high elastic limit material such as Eligoy. The stent 103 may have a substantially cylindrical shape, enclosing an inner volume 119. An outer diameter and a length of the stent 103 can be adapted such that the stent can be inserted into an aorta or a pulmonary artery of a patient.

In some embodiments, the stent 103 can be self-expandable. In such embodiments, the stent 103 may have an expanded configuration wherein the diameter of the stent is approximately equal to or slightly greater than a diameter of the blood vessel into which the stent 103 is to be inserted. For example, the stent 103 in the expanded configuration may have a diameter in a range from about 25 mm to about 45 mm. Hence, in the expanded configuration, the stent 103 may fit into the blood vessel, and may exhibit a slight pressure to the wall of the blood vessel, which may help to avoid a shifting of the stent 103. The stent 103 further may have a collapsed configuration wherein the stent 103 has a smaller diameter. The stent 103 may be brought into the collapsed configuration by radially compressing the stent 103, and may be held in the collapsed configuration by means of a sheath enclosing the stent 103, as will be explained in more detail below. If the sheath is removed, the stent 103 may return to its expanded configuration due to elastic forces. In some embodiments, the stent 103 can have a length in a range from about 80 mm to about 100 mm. A thickness of the stent 103 in the expanded configuration may have a value in a range from about 1 mm to about 2 mm.

In other embodiments, the stent 103 may be adapted for expansion from the collapsed configuration to an expanded configuration by means of an inflatable balloon provided in the inner volume 119 of the stent 103, as will be explained in more detail below.

The present invention is not restricted to embodiments wherein the stent 103 comprises a wire, as described above. In other embodiments, the stent 103 can have a substantially tubular configuration and may be formed from a plastic material. In such embodiments, the stent 103 may comprise a plurality of openings formed in its sidewalls.

The endovascular portion 101 further comprises an inflatable element 104. The inflatable element 104 may comprise an elastic envelope 308 enclosing an inner volume 307 of the inflatable element 104 (FIGS. 3a to 3d). A fluid line 105 may connect the inner volume 307 of the elastic envelope 308 to the extravascular portion 102 of the cardiac assist device 100. The elastic envelope 308 may comprise an elastic material, for example a polymer material such as silicone, polyurethane or gore-tex. A surface of the elastic envelope can be covered by a polymer and/or gore-tex to provide a smooth surface of the implantable element 104.

The inflatable element 104 can be provided in the inner volume 119 of the stent 103. The inflatable element 104 may have a substantially cylindrical configuration, wherein an outer diameter of the inflatable element 104 may be substantially identical to an inner diameter of the stent 103. The inflatable element 104 may enclose a central opening 104 being parallel to a longitudinal axis of the stent 103.

Figure 3A:
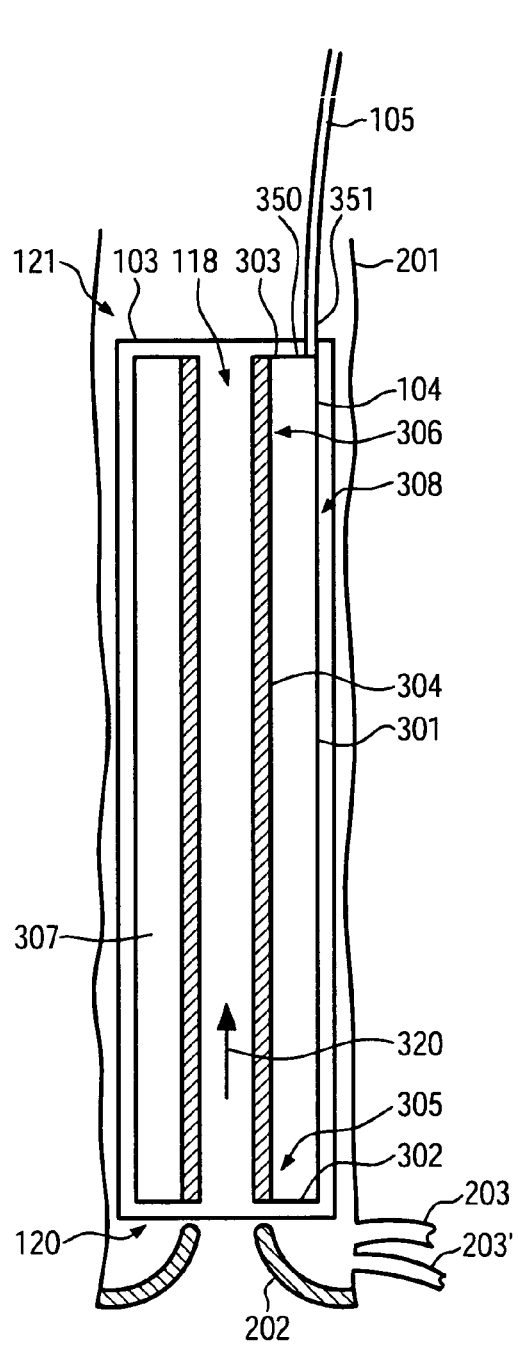
Figure 3B:
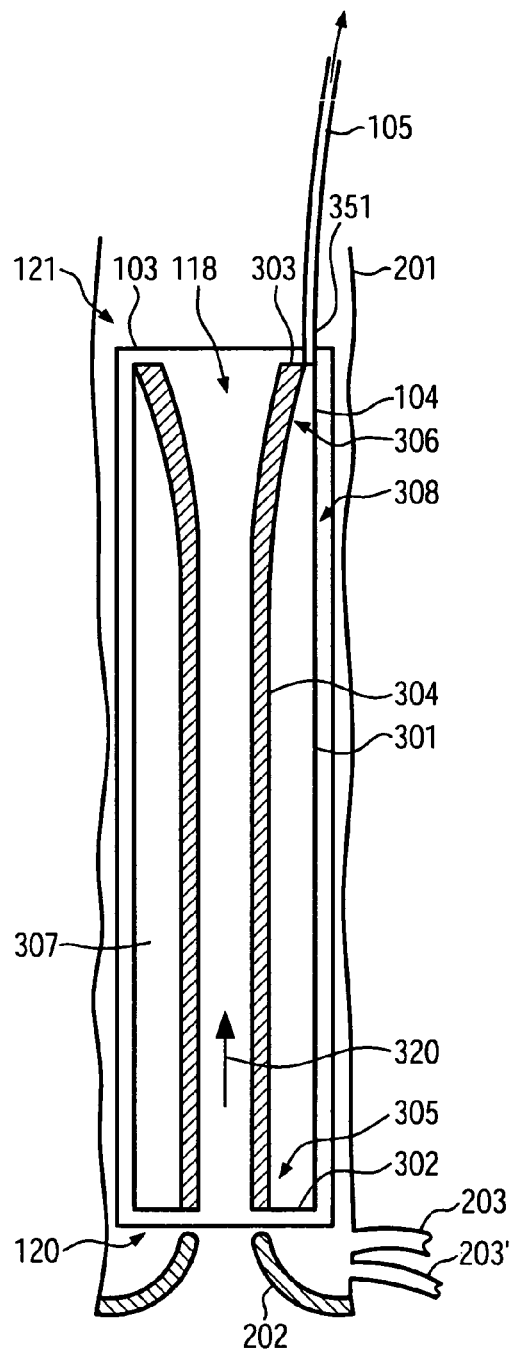

As shown in the cross-sectional views of FIGS. 3a to 3c, the elastic envelope 308 of the inflatable element 104 may comprise an outer circumferential portion 301 which can be attached to the stent 103, for example by means of gluing, high temperature gluing or shrink-wrapped polyurethane elements and an inner circumferential portion 304 enclosing the central opening 104. The inner circumferential portion 304 is connected to the outer circumferential portion 301 by a first cover portion 302 and a second cover portion 303.

As shown in FIGS. 3a to 3c, the fluid supply line 105 can be attached to the second cover portion 303. At least in the inflated state of the inflatable element 104, an area 350 of the second cover portion 302 adjacent the fluid supply line 105 may be substantially perpendicular to the longitudinal axis of the stent 103, and a portion 351 of the fluid supply line 105 adjacent the second cover portion 302 may be substantially parallel to the longitudinal axis of the stent 103. Thus, the fluid supply line 105 may extend along the aorta 201 of the patient, wherein the fluid supply line 105 is bent to a small extent only. In the deflated state of the inflatable element 204, the shape of the elastic envelope 308 may change to a certain extent. The portion 351 of the fluid supply line 105, however, may also extend along the aorta 201 in the deflated state while being bent only to a small extent.

The inner circumferential portion 304 of the elastic envelope 308 may comprise a first portion 305 adjacent a first end 120 of the stent 103 and a second portion 306 adjacent a second end 121 of the stent 103, wherein the first portion 305 has a higher degree of elasticity than the second portion 306. Due to the higher degree of elasticity of the first portion 305 of the inner circumferential portion 304 of the elastic envelope 308, the first portion 305 may be deformed to a greater extent than the second portion 306 if a pressure difference exists between the inner volume 307 of the elastic envelope and the exterior of the elastic envelope 308.

In some embodiments, the higher degree of elasticity of the first portion 305 of the inner circumferential portion 304 of the elastic envelope 308 may be created by providing the inner circumferential portion 304 with a smaller thickness adjacent the first end 120 of the stent 103 than adjacent the second end 121 of the stent 103. In one embodiment, the thickness of the inner circumferential portion 304 may increase continuously between the first end 120 and the second end 121 of the stent 103. In other embodiments, the thickness of the elastic envelope 308 at the inner circumferential portion 304 may be substantially equal throughout the first portion 305, and may be substantially equal throughout the second portion 306, wherein the thickness in the first portion 305 is smaller than the thickness in the second portion 306. In such embodiments, the thickness of the elastic envelope 308 may increase in a step-like manner at the boundary between the first portion 305 and the second portion 306.

The present invention is not restricted to embodiments wherein the first portion 305 and the second portion of the inner circumferential portion 304 of the elastic envelope 308 have a different thickness. In other embodiments, a higher degree of elasticity may be provided by forming the first portion 305 and the second portion from different materials. In still further embodiments, the degree of elasticity of the first portion 305 and the second portion 306 may be substantially the same.

The cardiac assist device 100 may further comprise a heartbeat detector 106. The heartbeat detector 106 may be attached to the stent 103, for example in the vicinity of the first end 120 of the stent 103. An electrical connection 107 which may, for example, comprise one or more electrically insulated wires may connect the heartbeat detector 106 to the extravascular portion 102 of the cardiac assist device 100. The electrical connection 107 may be used to supply power to the heartbeat detector 106 and to transmit signals from the heartbeat detector 106 to the extravascular portion 102 of the cardiac assist device 100.

The heartbeat detector can be configured to detect a cardiac action of the patient wearing the cardiac assist device. In some embodiments, the heartbeat detector 106 may comprise a flow sensor adapted to detect a flow speed of blood in the vicinity of the heartbeat detector. The flow speed of blood may exhibit periodic variations in time with the heartbeat of the patient. In other embodiments, the heartbeat detector 106 may comprise a pressure sensor and/or an electrocardiogram sensor detecting pressure variations and variations of an electric potential representative of the patient's heartbeat, respectively. For the purposes of the present invention, any type of flow sensor, pressure sensor and electrocardiogram sensor known to persons skilled in the art may be used. In embodiments of the present invention wherein the heartbeat detector 106 comprises a pressure sensor, the heartbeat detector 106 may be configured to detect an arterial and/or venous pressure curve.

The extravascular portion 102 may comprise a container 108 configured to protect an interior of the container 108 from bodily fluids of a patient into whose body the extravascular portion 108 is implanted. In one embodiment, the container 108 may comprise a biocompatible material such as, for example, titanium or a plastic material.

The container 108 may comprise components of a fluid supply adapted to periodically inflate and deflate the inflatable element 104 by periodically supplying a fluid to the inflatable element 104 and removing the fluid from the inflatable element 104 via the fluid line 105. Thus, the inflatable element 104 may periodically expand and contract in time with the supply and removal of the fluid.

The fluid may comprise a gas, for example helium, nitrogen and/or carbon dioxide. In other embodiments, the fluid may comprise a liquid such as water and/or a saline solution. A composition of the fluid may be selected such that a poisoning of the patient may substantially be avoided in case of a leakage of the fluid.

The fluid supply may comprise a pump 110 connected to the fluid line 105. Additionally, the fluid supply may comprise a power supply comprising a battery 113, a control unit 112 adapted to control the operation of the pump 110 and a fluid reservoir 111.

In some embodiments, the pump 110 may comprise a pneumatic micropump of a type known to persons skilled in the art. The pump 110 can be adapted to pump the fluid from the fluid reservoir 111 into the fluid line 105 connected to the inflatable element 104 to inflate the inflatable element 104, and from the fluid line 105 back into the fluid reservoir 111 to deflate the inflatable element 104.

The fluid reservoir 111 can comprise a vessel for storing the fluid. In some embodiments, the vessel can be configured to store the fluid under pressure. In such embodiments, the vessel may be formed from a rigid material such as, for example, a metal to withstand the pressure. In other embodiments, the vessel may be formed from an elastic material such as, for example, silicone, rubber or a plastic material. Thus, the vessel may expand when fluid is pumped into the vessel, and may contract when fluid is pumped out of the vessel. In such embodiments, a pressure obtained in the vessel during the operation of the pump 110 may be relatively low. Thus, an amount of energy required for the operation of the pump 110 may be reduced.

The fluid reservoir 111 can be adapted to store an amount of the fluid being greater than an amount required to completely inflate the inflatable element 104. Hence, a fluid reserve may be stored to compensate fluid losses which may be caused by leaks in the cardiac assist device 100.

The control unit 112 may be connected to the pump 110, and may further be connected to the heartbeat detector 106 via the electrical connection 107. Thus, the control unit 112 may receive signals from the heartbeat detector 106 to adapt the operation of the pump 110 to the heartbeat of the patient. In particular, the control unit 112 can be adapted to synchronize the periodic inflation and deflation of the inflatable element 104 with the cardiac action of the patient, as will be explained in more detail below.

The control unit 112 can comprise a microcontroller of a type known to persons skilled in the art. Additionally, the control unit 112 can comprise further electronic components such as switches for opening and closing an electrical connection between the battery 113 and the pump 110. Furthermore, the control unit 112 can comprise electronic equipment such as a sender and/or receiver for data transmission between the control unit 112 and a communication device which may be provided outside the patient's body. Thus, a doctor may monitor the operation of the cardiac assist device 100 while it is implanted into the patient, and/or may configure the cardiac assist device 100 to better adapt its operation to the specific needs of the patient.

In addition to the battery 113, the power supply may comprise an induction coil 114. In some embodiments, the induction coil 114 may comprise a wire formed from an electrically conductive material such as copper and wound into a spiral shape on a plate 109. The wire may be covered by an electrically insulating material to avoid electric shortcuts resulting from a contact between the wire and electrically conductive bodily fluids of the patient. The induction coil 114 can be electrically connected to the battery 113 which may, in such embodiments, be rechargeable, and/or the control unit.

The induction coil 114 and the plate 109 may subcutaneously be implanted into the patient. An electric current in the induction coil 114 may inductively be generated by providing an external coil outside the body in the vicinity of the induction coil 114 and applying an alternating current to the external coil. The current may be used to recharge the battery 113. In the container 108, components such as a transformer and/or a rectifier may be provided to adapt the electrical current for recharging the battery 113. Hence, the battery 113 can be recharged in a convenient manner.

In the following, the implantation of the cardiac assist device will be described with reference to FIGS. 2a to 2c.

Figure 2A:
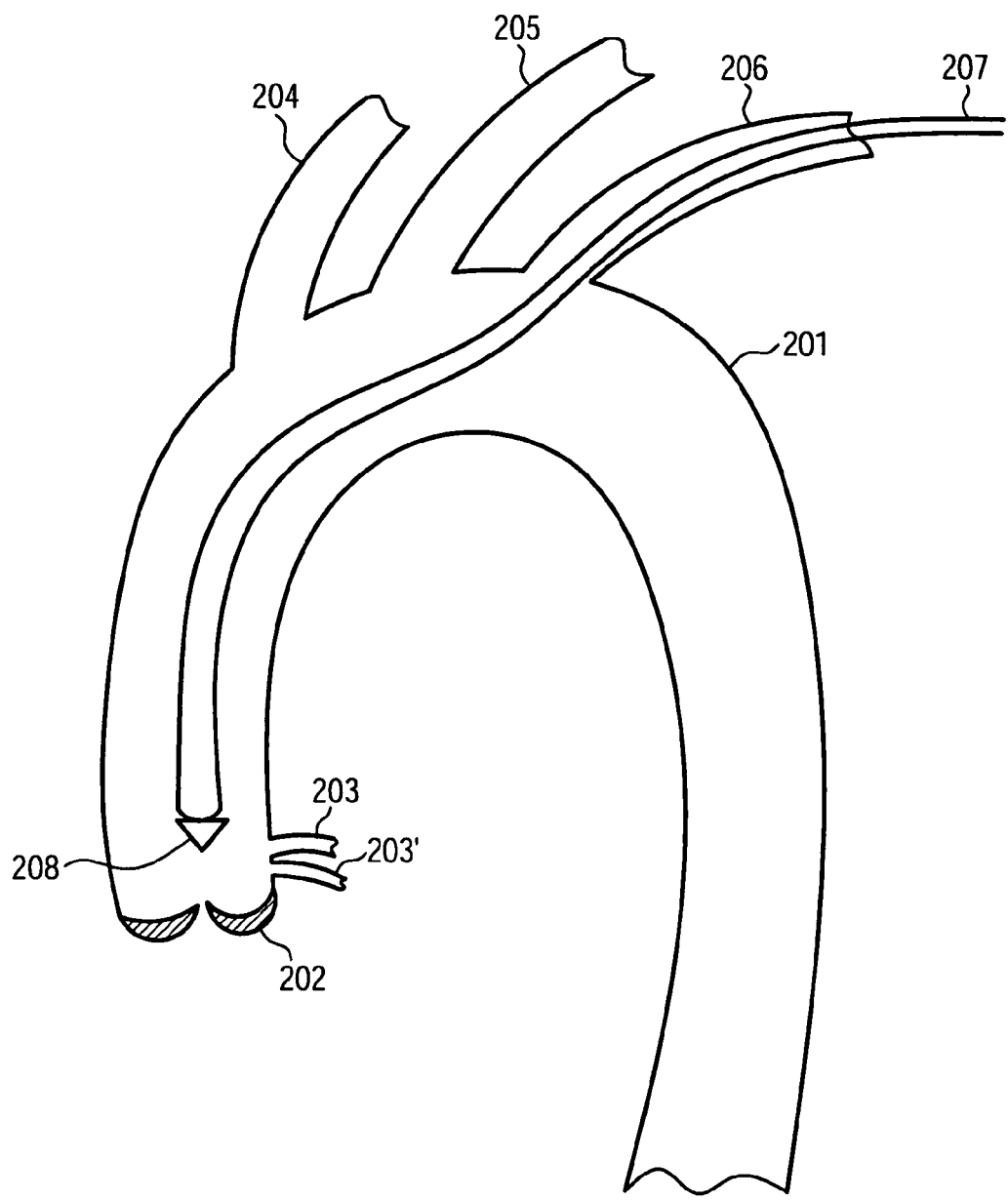
FIGS. 2a to 2c show schematic views of an aorta in stages of a method of inserting a cardiac assist device according to an embodiment of the present invention.
Figure 2B:
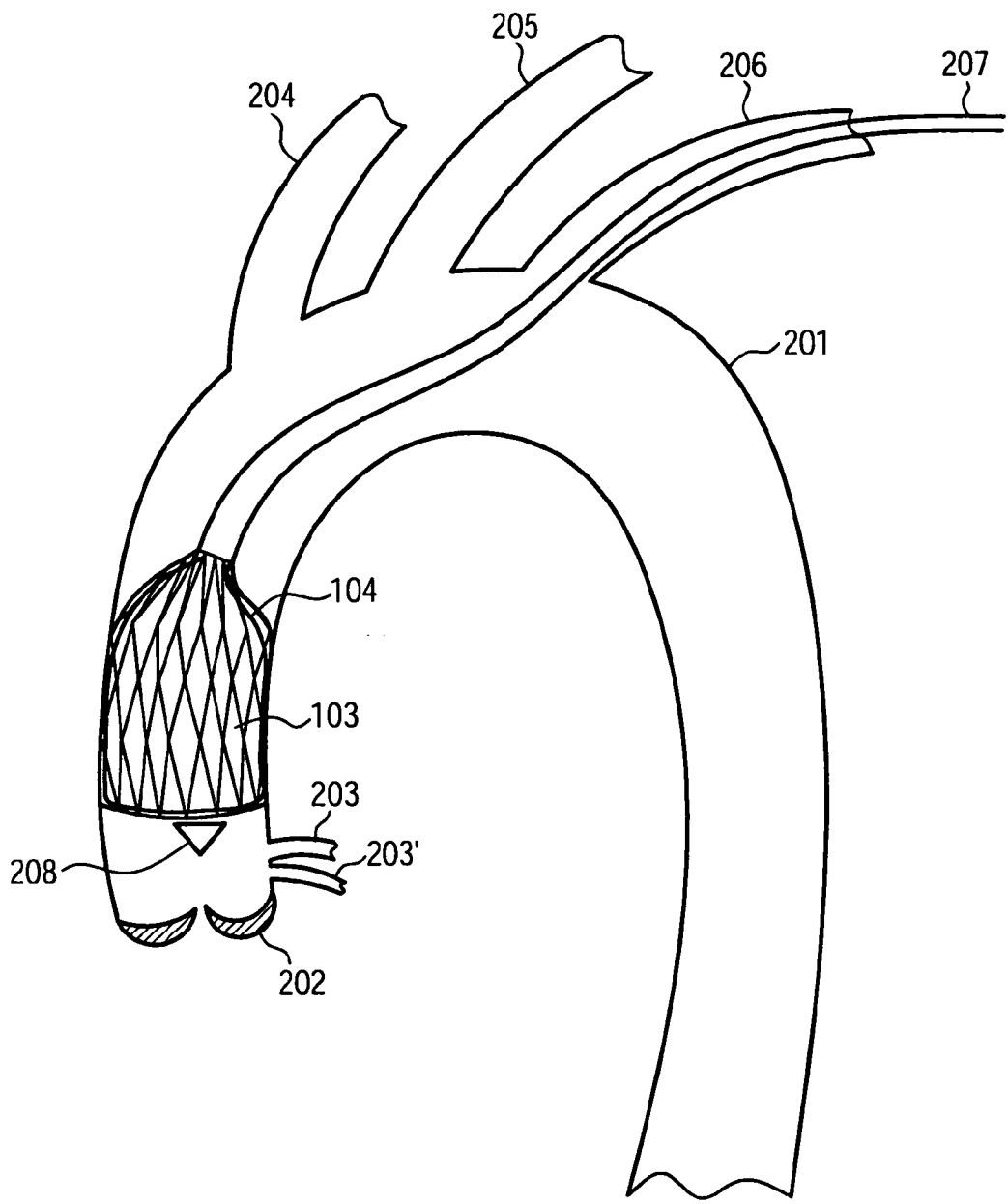
Figure 2C:
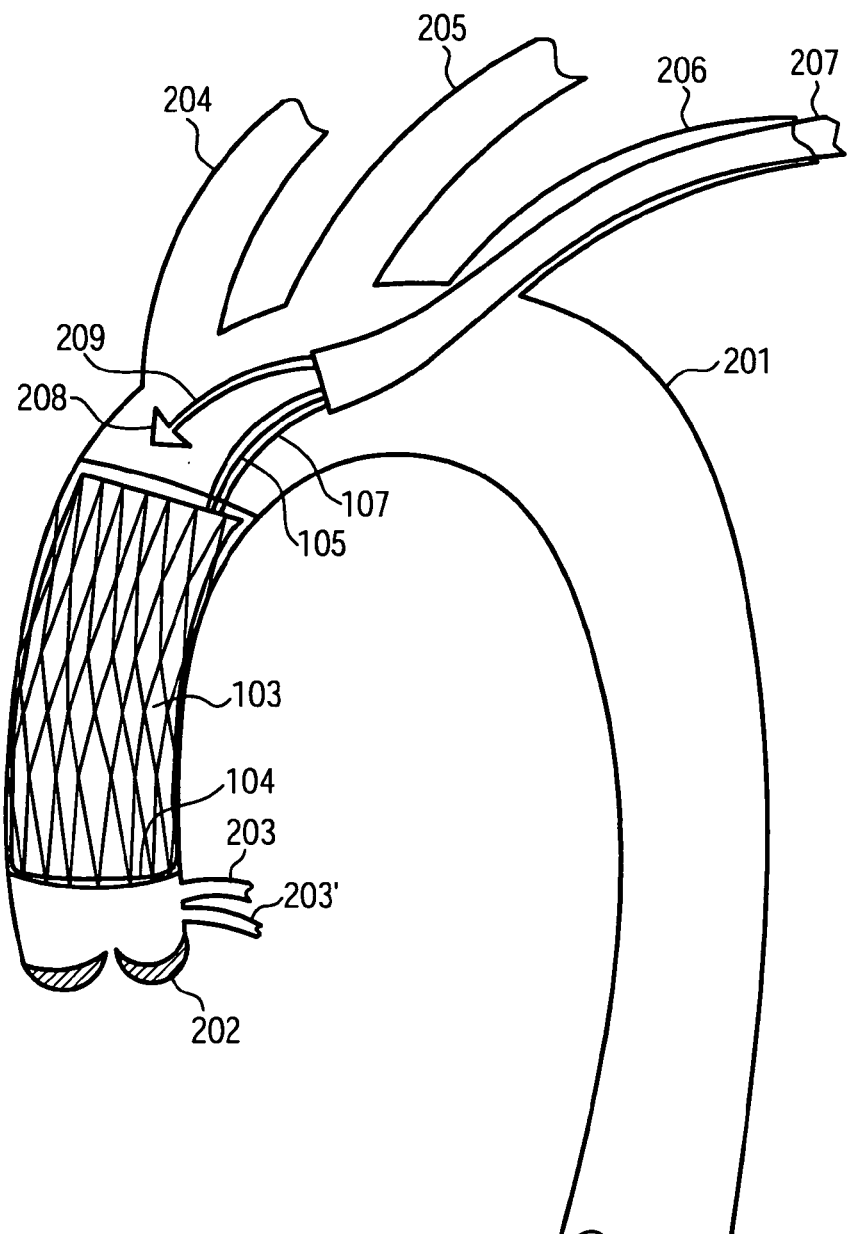

FIGS. 2a to 2c shows schematic view of an aorta 201 of a patient in stages of a method of implanting the cardiac assist device 100. In FIGS. 2a to 2c, reference numeral 202 denotes an aortic valve, reference numerals 203, 203' denote the right coronary artery and the left coronary artery, respectively, reference numeral 204 denotes the innominate artery, reference numeral 205 denotes the left common carotid artery and reference numeral 206 denotes the subclavian artery. As persons skilled in the art know, the left ventricle of the patient's heart is located adjacent the aortic valve 202 and pumps blood into the aorta 201.

The endovascular portion 101 of the cardiac assist device 100 may be implanted into the ascending part of the aorta 201, beginning about 10 to 15 mm above the aortic valve 202 up to about 5 mm under the offspring of the innominate artery 204, as shown schematically in FIG. 2c. Thus, the cardiac assist device 100 may be used to support the left ventricle of the patients heart. The present invention, however, is not restricted to embodiments wherein the cardiac assist device 100 is implanted into the aorta 201. In other embodiments, the endovascular portion 101 can be implanted into the pulmonary artery of the patient, beginning about 10 to 15 mm above the pulmonary valve up to about 5 mm under the first offspringing branch of the pulmonary artery to assist the right ventricle of the patient's heart.

To implant the endovascular portion 101 of the cardiac assist device 100, a catheter 209 may be used. A configuration of the catheter 209 may be similar to a configuration of heart catheters known to persons skilled in the art. In particular, the configuration of the catheter 209 may be similar to that of a known catheter adapted for the insertion of an aortic stent adapted for the treatment of an aortic dissection.

The catheter 209 may run through the central opening 118 of the inflatable element 104, and through the stent 103. During the insertion of the endovascular portion 101, the stent 103 can be in the collapsed configuration, and the inflatable element 104 may be deflated. Hence, during the insertion of the endovascular portion 101, the diameter of the endovascular portion 103 may be relatively small to allow a motion of the endovascular portion through blood vessels of the patient. A sheath 207 may be provided over the endovascular portion 101 of the cardiac assist device 100. The sheath 207 may maintain the stent 103 in the collapsed configuration as long as the stent 103 is covered by the sheath. Additionally, the sheath 207 may be marked for x-ray imaging. Moreover, the fluid line 105 and the electrical connection may run through the sheath 207. A nose cone 208 may be provided at the tip of the catheter 209. The nose cone 208 may have a diameter which is equal to or slightly greater than the inner diameter of the stent 103 in the collapsed configuration, and may help to avoid a premature sliding of the endovascular portion 101 off the catheter 209.

The catheter 209 may be inserted into a peripheral artery of the patient by means of the Seldinger technique which is well known to persons skilled in the art. Thereafter, the catheter 209 can be advanced into the aorta of the patient such that the nose cone 208 is located in the vicinity of the aortic valve 202, as shown in FIG. 2a.

FIG. 2b shows a schematic view of the aorta 201 in a later stage of the insertion of the endovascular portion 101 of the cardiac assist device 101. After the catheter 209 has been advanced to the vicinity of the aortic valve 202, the sheath 207 may be withdrawn to expose the endovascular portion 101. As the sheath 207 is removed, portions of the stent 103 which are not covered by the sheath 207 any more, may change from the collapsed configuration into the expanded configuration. As already explained above, the outer diameter of the stent 103 in the expanded configuration may be selected to be equal to or slightly greater than the inner diameter of the patient's aorta 201 such that the stent 103 is attached to the aorta 201 by friction.

The present invention is not restricted to embodiments wherein the stent 103 is self-expandable such that the stent 103 changes into the expanded configuration as soon as the sheath 207 is removed. In other embodiments, the stent 103 can be adapted such that it may remain in the collapsed configuration after the removal of the sheath 207. In such embodiments, the stent 103 may be expanded by means of a balloon element (not shown) provided in the inner volume 119 of the stent and attached to the catheter 209, which is inflated after the removal of the sheath 207. In further embodiments, the stent 103 may be expanded by inflating the inflatable element 104 by supplying fluid through the fluid line 105.

FIG. 2c shows a schematic view of the aorta 201 in yet another stage of the insertion of the endovascular portion 101 of the cardiac assist device 101, wherein the sheath 207 has been completely removed from the stent 103. Hence, the stent 103 is in the expanded configuration and is attached to the aorta 201. After removing the sheath 207 from the stent 103, the sheath 207 may be retracted further to expose the fluid line 105 and the electrical connection 107. Thus, the fluid line 105 and the electrical connection 107 may be implanted into blood vessels of the patient. Thereafter, the catheter 209 may be retracted. If the stent 103 does not fit exactly to the aorta 201, a manual balloon may be used to slightly expand the stent 103.

Before or after the insertion of the endovascular portion 101 of the cardiac assist device 100, the extravascular portion 102 may also be implanted into the patient. This can be done by means of methods of surgery well known to persons skilled in the art. In one embodiment, the container 108 can be pectorally implanted, and the induction coil 114 may be implanted at the lateral aspect of the chest. Moreover, the fluid line 105 and the electrical connection 107 may be connected to the pump 110 and the control unit 112, respectively. Thereafter, the operation of the cardiac assist device 100 may be initiated.

In some embodiments, the size of the ascending part of the aorta 201 may be measured before the insertion of the endovascular portion 101, and an appropriate endovascular portion 101 may be selected on the basis of the measurement. The measurement can be performed by means of techniques known to persons skilled in the art such as x-raying, for example multislice computer tomography and/or three-dimensional computer tomography, wherein, in some embodiments, a contrast agent may be employed.

To insert the endovascular portion 101 into the subclavian artery 206, an incision may be made about 10 to 20 mm below the clavicle near the groove. As an alternative to the Seldinger technique described above, the lower surface of the subclavian artery 206 may be prepared, and a 6/0 pursestring suture can be made to introduce the endovascular portion 101 and the catheter 209 covered by the sheath 207 via an incision of the subclavian artery 206. Using a catheter guide of a type known to persons skilled in the art, the endovascular portion 101 may then be positioned in the aorta 201, as described above.

In embodiments wherein the endovascular portion 101 is inserted into the pulmonary artery of the patient, the endovascular portion 101 and the catheter 209 covered by the sheath 207 can be inserted into the pulmonary artery via the subclavian vein and the right ventricle of the patient's heart.

In embodiments wherein the stent 103 is expanded by inflation of the inflatable element 104, a balloon dilatation and/or percutaneous coronary intervention may be performed if the stent 103 is not accurately expanded to fix the endovascular portion 101 at a desired position.

In further embodiments, the endovascular portion 101 may be inserted by means of a median sternotomy and a pursestring suture at the distal part of the ascending aorta. The stent 103, the inflatable element 104 and the heartbeat detector 106 may be inserted through an incision in the aorta. In such embodiments, a catheter and a sheath similar to the catheter 209 and the sheath 207 may be used to insert the fluid supply line 205 and the electrical connection 107 via a peripheral blood vessel of the patient. The fluid supply line 205 and the electrical connection 107 may subsequently be grasped through the incision in the aorta and can then be connected to the inflatable element 104 and the heartbeat detector 106.

To implant the extravascular portion 102, a subcutane or subpectoral pocket may be formed in the subclavicular region. For this purpose, techniques similar to those used in the implantation of a pacemaker or implantable cardioverter-defibrillator may be employed, and the container 108 can be inserted into the pocket.

Additionally, a further subcutane pocket can be formed below the pocket in the subclavicular region at a subaxillar position at the lateral aspect of the thorax and/or in the lateral epigastric region, and the induction coil 104 and the plate 109 can be inserted therein.

In the following, the operation of the cardiac assist device will be described with reference to FIGS. 3a to 3d.

FIGS. 3a to 3d show schematic cross-sectional views of the ascending part of the aorta 201 of the patient. The cardiac assist device 100 is inserted into the aorta 201 above the right coronary artery 203 and the left coronary artery 203' and below the innominate artery 204 (not shown in FIGS. 3a to 3d), as described above with reference to FIGS. 2a to 2c.

The inflatable element 104 can be periodically inflated and deflated. The inflation and deflation of the inflatable element 104 can be synchronized with the cardiac action of the patient, which may be detected by means of the heartbeat detector 106. In some embodiments, the inflatable element 104 can be deflated during systole, and may be inflated during diastole.

FIG. 3a shows a cross-sectional view of the aorta 201 during systole, immediately after the aortic valve 202 has opened. At this point of time, the inflatable element 104 may be substantially completely inflated. Hence, the inflatable element 104 may occupy a relatively large amount of space in the patient's aorta, and the central opening 118 of the inflatable element 104 may have a relatively small diameter. Blood ejected by the left ventricle of the patient's heart may flow through the central opening 118, as indicated by arrow 320 in FIG. 3a.

FIG. 3b shows a cross-sectional view of the aorta 201 at a later point of time during systole. During the systole, which may be detected by means of the control unit 112 and the heartbeat detector 106, the pump 110 may be activated to deflate the inflatable element 104 by pumping fluid out of the inflatable element 104. Therefore, the pressure in the inflatable element 104 and a volume occupied by the inflatable element 104 in the aorta 201 can be reduced. Since the outer circumferential portion 301 of the elastic envelope 308 is attached to the stent 103, the reduction of the volume of the inflatable element 104 may comprise an increase of the diameter of the central opening 118 of the inflatable element.

In embodiments of the present invention wherein the first portion 305 of the inner circumferential portion 304 of the elastic envelope 308 comprises a higher degree of elasticity than the second portion 306, the decreasing pressure in the inner volume 307 of the inflatable element 104 may overcome the stronger mechanical forces exhibited by the less stretchable second portion 306 to a less extent than the mechanical forces exhibited by the first portion 305. Therefore, a diameter of the central opening 118 may first increase adjacent the second end 121 of the stent 103. Hence, the central opening 118 may obtain a substantially conical shape. As the deflation of the inflatable element 104 continues, the diameter of the inflatable element 104 may also be reduced in the first portion 305 of the inner circumferential portion 304 of the elastic envelope 308.

Due to the reduction of the volume of the inflatable element 104, a vacuum may be created in the aorta 201 in the vicinity of the heart valve 202. Due to this vacuum, blood may be drawn through the aortic valve 202 into the central opening 118 of the inflatable element 104. Hence, the deflation of the inflatable element may assist the ejection of blood by the patient's ventricle. Thus, an afterload which must be overcome by the ventricle to eject blood may significantly be reduced.

FIG. 3c shows a schematic cross-sectional view of the aorta 201 and the endovascular portion 101 of the cardiac assist device 100 at the end of the systole. At this point of time, the inflatable element 104 can be in a substantially deflated state such that the inflatable element occupies only a relatively small volume in the aorta 201 and the central opening 118 of the inflatable element 104 is relatively large. The aortic valve 202 may be substantially completely closed, since the ejection of blood out of the ventricle is substantially completed.

FIG. 3d shows a schematic cross-sectional view of the aorta 201 and the endovascular portion 101 of the cardiac assist device 100 during diastole. At the beginning of the diastole, which may be detected by means of the heartbeat detector 106 and the control unit 112, the control unit 112 may activate the pump 110 to pump fluid into the inflatable element 104 via the fluid line 105 to inflate the inflatable element 104. In some embodiments of the present invention, the inflatable element 104 may be inflated until a pressure of about $2.67 \cdot 10^4$ Pa (200 mm Hg) is obtained in the inflatable element 104. In such embodiments, the pressure in the inflatable element 104 may be sensed by means of a pressure sensor provided in the inflatable element 104 and/or in the container 108 in the vicinity of the pump 110.

Due to the inflation of the inflatable element 104, a volume occupied by the inflatable element 104 in the aorta 201 may increase, and a diameter of the central opening 118 of the inflatable element 104 may decrease. Therefore, the inflatable element may push blood which was ejected by the patient's ventricle during systole out of the portion of the aorta 201 which is occupied by the endovascular portion 101 of the cardiac assist device 100. The aortic valve 202 of the patient may substantially prevent a flow of blood back into the ventricle. Therefore, a blood flow into the left coronary artery 203 and the right coronary artery 203', as well as a blood flow through the aorta 201 in a direction away from the aortic valve 202, into the circulatory system of the patient, can be obtained.

In embodiments of the present invention wherein the first portion 305 of the inner circumferential portion 304 of the elastic envelope 308 comprises a higher degree of elasticity than the second portion 306, the diameter of the central opening 118 may first be reduced in the vicinity of the first end 120 of the stent 103, which can be provided adjacent the aortic valve 201. As the pressure in the inflatable element 104 is further increased, the diameter of the central opening 118 may also increase in the second portion 306 of the inner circumferential portion 304 of the elastic envelope 308. Thus, a column of blood located in the central opening 118 of the elastic element 104 can be pushed upward into the aorta 201. This may help to reduce a pressure exhibited on the aortic valve 202.

At the end of the diastole, the inflatable element 104 may be substantially completely inflated, having a configuration similar to that shown in FIG. 3a. During the subsequent systole and diastole, the cycle described above may be repeated.

The amount of blood in the central opening 118 of the inflatable element 104 which is pushed into the circulatory system of the patient during diastole may be estimated as $$V = 2\pi r^2 h$$

wherein r denotes a diameter of the aorta 201 and h denotes a length of the inflatable element. Since the diameter of a normal aorta may be about 30 mm or more, and the length of the inflatable element 104 may be about 100 mm, the amount V may be estimated as being about 70.65 ml or more. Hence, with a heart rate varying from about 70 to about 100 beats per minute, about 4900 ml to about 7000 ml may be pumped into the circulatory system of the patent by the cardiac assist device 100.

A cardiac output during systole can be influenced by three main factors:
 1. Preload;
 2. Afterload; and
 3. Contractibility.

While the presence of the cardiac assist device 100 according to the present invention may have a relatively small influence on the preload, the contractibility of the ventricle of the patient's heart may be improved, since blood can be pumped into the right coronary artery 203 and the left coronary artery 203' during the inflation of the inflatable element 104, such that an oxygenation of the myocardium may be improved.

Moreover, as detailed above, the afterload may be significantly reduced by the cardiac assist device according to the present invention, since blood may be sucked out of the ventricle as the inflatable element 104 is deflated during systole. Hence, the cardiac assist device 100 according to the present invention may help to increase the cardiac output.

A compromised left ventricle may have a cardiac output of about 2 to about 2.5 l/min or less. Assuming a patient in terminal heart failure with a cardiac output of 1.5 l/min and a heart rate of 80 beats per minute, the cardiac output obtained when using the cardiac assist device 100 according to the present invention may be estimated as follows:
1. An increase of cardiac output during systole to about 2.0 l/min due to the improved contractibility; and
2. An additional output of about 5.6 l/min (80 times about 70 ml) provided by the pumping effect of the periodic inflation and deflation of the inflatable element 104.

Hence, in a patient whose life might be hard to save even by means of a heart transplant, a total cardiac output of about 7.6 l/min may be obtained, which may be even slightly more than a normal cardiac output. During activity of the patient, the heart rate might increase to about 120 beats per minute. Hence, a cardiac output of about 11.4 l/min can be obtained, which may be sufficient for a moderate to severe physical activity.

Further embodiments of the present invention will be described with reference to FIG. 4.

Figure 4:
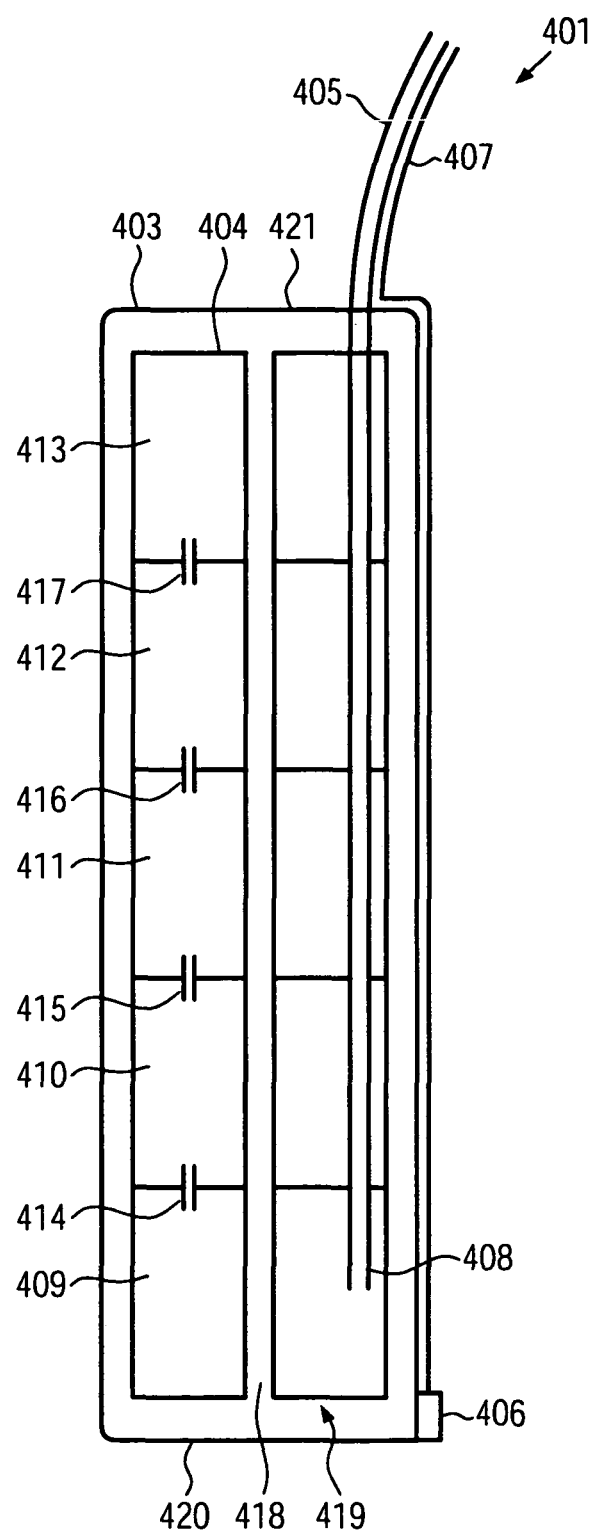
FIG. 4 shows a schematic cross-sectional view of a portion of a cardiac assist device according to another embodiment of the present invention.

FIG. 4 shows a schematic cross-sectional view of an endovascular portion 401 which may be provided in the cardiac assist device 100 instead of the endovascular portion 101 described above.

The endovascular portion 401 comprises a stent 403, which may comprise features similar to those of the stent 103 described above. Similar to the embodiments described above, a heartbeat detector 406 can be provided at the first end 420 of the stent 403. An electrical connection 407 may connect the heartbeat detector 406 to the control unit 112.

In an inner volume 419 of the stent 403, an elastic envelope 404 is provided. The elastic envelope 404 may comprise an elastic material such as, for example, silicon. The elastic envelope 404 may comprise a plurality of inflatable elements 409, 410, 411, 412, 413 provided in form of chambers formed in the elastic envelope 404 which are arranged in a row along a longitudinal direction of the stent 403. Hence, a first inflatable element 409 may be provided adjacent a first end 420 of the stent 403, and a last inflatable element 413 may be provided adjacent a second end 421 of the stent 403. Between the first inflatable element 409 and the last inflatable element 413, intermediary inflatable elements 410-412 can be provided. If the endovascular portion 401 is implanted into a blood vessel of a patient, the first end 420 of the stent 403 may be provided adjacent a heart valve of the patient.

A fluid line 405 can be connected to the pump 110, and may be adapted to supply a fluid to the elastic envelope 404 and to remove fluid from the elastic envelope 404 for inflation and deflation of the inflatable elements 409-413.

An end 408 of the fluid line 405 may be provided in the first inflatable element 409. Hence, fluid may be pumped into the first inflatable element 409 and out of the first inflatable element 409 by operating the pump 110. Between each pair of adjacent ones of the inflatable elements 409-413, a flow restrictor which may, for example, comprise an orifice, can be provided. Hence, if fluid is pumped into the fluid line 405, the fluid may flow from the first inflatable element 409 into the inflatable element 410 via flow restrictor 414, from the inflatable element 410 into the inflatable element 411 via flow restrictor 415, from the inflatable element 411 to the inflatable element 412 via flow restrictor 416, and from the inflatable element 412 into the last inflatable element 413. Hence, the inflatable elements 409-413 may be inflated successively, since the flow restrictors 414-417 may slow down fluid flow between the inflatable elements 409-413. If fluid is pumped out via the fluid line 405, the inflatable elements 409-411 can be deflated successively, since fluid flow between the inflatable elements 409-411 can be slowed down by the flow restrictors 414-417. Thus, the inflatable elements 409-411 may be successively inflated and deflated to actively move blood located in a central opening 418 of the inflatable element 404 into a desired direction.

The present invention is not restricted to embodiments wherein flow restrictors 414-417 are provided between adjacent ones of the inflatable elements 409-413. In other embodiments, the inflatable elements 409-413 may be sealed against fluid communication between the inflatable elements 409-413, and an individual fluid line may be connected to each of the inflatable elements 409-413. Each of the fluid lines may be connected to an individual pump provided in the container 108. Hence, each of the inflatable elements 409-413 may individually be inflated and deflated. This may allow a more precise control of the inflation and deflation of the inflatable elements 409-413.

In still further embodiments, a single fluid line may be provided, and a solenoid valve may be provided between the fluid line and each of the inflatable elements 409-413. The solenoid valves may be operated by means of an electric current supplied by electrical connections to the control unit 112. Hence, the inflatable elements 409-413 may be inflated and deflated individually by operation of the solenoid valves, whereas the single fluid line may advantageously require a smaller amount of space in the blood vessels of the patient than a plurality of fluid lines.

Moreover, the present invention is nor restricted to embodiments wherein five inflatable elements 409-413 are provided, as shown in FIG. 4. In other embodiments, a greater or smaller number of inflatable elements 409-413 can be provided.

The invention claimed is:

1. Cardiac assist device, comprising:
   a stent implantable in a blood vessel of a patient, said stent enclosing an inner volume;
   at least one inflatable element attached to said stent, said at least one inflatable element being provided in said inner volume of said stent, wherein said at least one inflatable element comprises an elastic envelope enclosing an inner volume of said at least one inflatable element, wherein the elastic envelope annularly encloses a central opening being parallel to a longitudinal axis of said stent and having a variable diameter; and
   a fluid supply comprising at least one fluid supply line connected to said inner volume of said elastic envelope of said at least one inflatable element and implantable into a blood vessel of said patient, the fluid supply being adapted for periodically inflating and deflating said at least one inflatable element by periodically supplying a fluid to and removing the fluid from said inner volume of said elastic envelope of said at least one inflatable element;
   said annular central opening not being in fluid communication with said inner volume of said elastic envelope of said at least one inflatable element.

2. Cardiac assist device according to claim 1, wherein, said elastic envelope comprises an inner circumferential portion enclosing said central opening, said inner circumferential portion having a higher degree of elasticity adjacent a first end of said stent than adjacent a second end of said stent.

3. Cardiac assist device according to claim 2, wherein said inner circumferential portion of said elastic envelope has a smaller thickness adjacent said first end of said stent than adjacent said second end of said stent.

4. Cardiac assist device according to claim 1, wherein said at least one inflatable element comprises a plurality of inflatable elements and wherein said fluid supply is adapted to successively inflate said plurality of inflatable elements and to successively deflate said plurality of inflatable elements.

5. Cardiac assist device according to claim 4, wherein said fluid supply is adapted to individually inflate and deflate each of said plurality of inflatable elements.

6. Cardiac assist device according to claim 1, further comprising a heartbeat detector adapted to detect a cardiac action of said patient.

7. Cardiac assist device according to claim 6, wherein said heartbeat detector comprises at least one selected from the group consisting of a flow sensor, a pressure sensor and an electrocardiogram sensor.

8. Cardiac assist device according to claim 6, wherein said fluid supply is adapted to synchronize said periodic inflation and deflation of said at least one inflatable element with said cardiac action of said patient.

9. Cardiac assist device according to claim 1, wherein said fluid supply comprises:
  at least one pump, said at least one fluid supply line connecting said at least one pump and said at least one inflatable element;
  a control unit adapted to control said pump to provide said periodic inflation and deflation of said inflatable element; and a power supply connected to said at least one pump and said control unit.

10. Cardiac assist device according to claim 9, wherein said fluid supply is implantable into said patient.

11. Cardiac assist device according to claim 10, wherein said power supply comprises a rechargeable battery, and said fluid supply further comprises an induction coil subcutaneously implantable into said patient for recharging said rechargeable battery.

12. Cardiac assist device according to claim 9, wherein said fluid supply further comprises a fluid reservoir.

13. Cardiac assist device according to claim 1, wherein said stent has a length in a range from 80mm to 100 mm and an outer diameter in a range from 25 mm to 45mm.

14. Cardiac assist device according to claim 1, wherein said stent is self-expandable.

15. Cardiac assist device according to claim 1, wherein said elastic envelope comprises an inner circumferential portion enclosing said central opening, an outer circumferential portion attached to said stent and a first and a second cover portion connecting said inner circumferential portion and said outer circumferential portion, wherein said at least one fluid supply line is attached to said second cover portion.

16. Cardiac assist device according to claim 15, wherein, at least in an inflated state of said at least one inflatable element, an area of said second cover portion adjacent said at least one fluid supply line is substantially perpendicular to said longitudinal axis of said stent.

17. Cardiac assist device according to claim 16, wherein a portion of said at least one fluid supply line adjacent said second cover portion is substantially parallel to said longitudinal axis of said stent.

18. Cardiac assist device according to claim 1, wherein said stent has a collapsed configuration and an expanded configuration, and wherein said cardiac assist device further comprises:
  a catheter running through said central opening of said stent; and
  a removable sheath adapted to maintain said stent in said collapsed configuration, wherein said at least one fluid supply line is running through said sheath; and
  wherein said catheter is adapted for being removed after removal of said sheath.

19. A method of providing cardiac assist to a patient, comprising:
  providing an endovascular portion of a cardiac assist device comprising a stent enclosing an inner volume, at least one inflatable element being attached to said stent and provided in said inner volume of said stent wherein said at least one inflatable element comprises an elastic envelope enclosing an inner volume of said at least one inflatable element, and a fluid supply line in fluid communication with said inner volume of said elastic envelope, wherein the elastic element annularly encloses a central opening parallel to a longitudinal axis of said stent, said central opening having a variable diameter, said central opening not being in fluid communication with said inner volume of said elastic envelope of said at least one inflatable element;
  implanting said endovascular portion into said patient, wherein said stent and said at least one inflatable element are provided in one of an aorta and a pulmonary artery of said patient, and wherein said fluid supply line extends from said one of said aorta and said pulmonary artery to a peripheral blood vessel of said patient;
  providing an extravascular portion of said cardiac assist device, said extravascular portion comprising a fluid supply;
  connecting said at least one fluid supply line to said extravascular portion; and
  operating said fluid supply to periodically inflate and deflate said at least one inflatable element by periodically supplying a fluid to and removing the fluid from said inner volume of said elastic envelope of said at least one inflatable element.

20. A method as in claim 19, further comprising implanting said extravascular portion into said patient.

21. A method as in claim 20, wherein at least a part of said extravascular portion is pectorally implanted into said patient.

22. A method as in claim 19, wherein said cardiac assist device is operated for at least two weeks.

23. A method as in claim 19, further comprising:
  providing a catheter running through said central opening of said inflatable element and through said stent,
  providing a sheath over said endovascular portion, said sheath being adapted to maintain said stent in a collapsed configuration, wherein said at least one fluid supply line is running through said sheath, and wherein said implantation of said endovascular portion comprises:
  inserting said catheter into said peripheral blood vessel of said patient;
  advancing said catheter to said one of said aorta and said pulmonary artery;
  withdrawing said sheath to expose said endovascular portion;
  expanding said stent into an expanded configuration; and
  retracting said catheter.

24. A method as in claim 23, wherein said sheath is retracted further to expose said fluid supply line.

25. A Cardiac assist device for assisting blood flow within a blood vessel comprising:

a stent having a longitudinal axis and an inner volume;

an inflatable tubular element attached to said stent, said inflatable tubular element being provided in the inner volume of said stent and having an outer circumferential portion attached to an inner circumferential portion of said stent, wherein said inflatable element moves annularly radially inward from the outer circumferential portion of said inflatable element forming a central opening without a closed end permitting blood to flow there through and having a variable inner diameter, the central opening being parallel to the longitudinal axis of said stent ; and a fluid supply, coupled to said inflatable element, capable of periodically inflating and deflating said at least one inflatable element, whereby the variable inner diameter of the central opening of said inflatable element is periodically radially reduced in size assisting blood flow.

26. A cardiac assist device for assisting blood flow within a blood vessel comprising:

a stent adapted to be implanted into the blood vessel, said stent having a bore and an inner bore circumferential surface;

an inflatable tubular element with a central opening without a closed end permitting blood to flow there through and having a variable inner diameter, the inflatable tubular element having a volume placed within the bore of said stent, said inflatable tubular element having an outer circumferential surface in contact with the inner bore circumferential surface formed by the bore within said stent and an inner opening circumferential surface forming the central opening; and a pump coupled to said inflatable tubular element, whereby when said inflatable tubular element is inflated by said pump the inner circumferential surface moves away from the outer circumferential surface reducing the volume of the variable inner diameter of the central opening thereby assisting blood flow.

* * * * *